United States Patent [19]

Maeda et al.

[11] 4,396,714

[45] Aug. 2, 1983

[54] N-SULFOALKYLANILINE DERIVATIVES

[75] Inventors: Masanobu Maeda; Yuko Murao, both of Kumamotoshi, Japan

[73] Assignee: Dojindo Laboratories, Japan

[21] Appl. No.: 278,321

[22] Filed: Jun. 29, 1981

Related U.S. Application Data

[62] Division of Ser. No. 198,279, Oct. 17, 1980, abandoned.

[30] Foreign Application Priority Data

Jan. 9, 1980 [JP] Japan ................................. 55-711
Mar. 25, 1980 [JP] Japan ................................. 55-38630

[51] Int. Cl.$^3$ .................. C12Q 1/28; C12Q 1/54;
C12Q 1/60; C12Q 1/62; G01N 33/48
[52] U.S. Cl. ........................................ 435/28; 435/10;
435/11; 435/12; 435/14; 435/20; 436/64;
436/71; 436/74; 436/84; 436/95; 436/99;
436/135; 260/508; 260/509
[58] Field of Search .................. 23/230 B, 230 R;
435/28, 20, 10, 11, 12, 14; 252/408; 436/64, 71,
74, 84, 99, 95, 135; 260/508, 509

[56] References Cited

U.S. PATENT DOCUMENTS

| | | | |
|---|---|---|---|
| 2,241,769 | 5/1941 | Dickey et al. | 260/509 |
| 2,319,078 | 5/1943 | McNally et al. | 260/509 |
| 2,323,714 | 7/1943 | Kirby et al. | 260/509 |
| 2,402,538 | 6/1946 | Dreyfus | 260/509 |
| 3,870,696 | 3/1975 | Freeman | 260/508 |
| 3,971,769 | 7/1976 | Feeman | 260/508 |
| 4,054,147 | 10/1977 | Kalopissis et al. | 8/10 |
| 4,066,408 | 1/1978 | Jonsson et al. | 435/28 |
| 4,247,631 | 1/1981 | Nix et al. | 435/28 |
| 4,251,629 | 2/1981 | Yamanisi et al. | 252/408 |
| 4,260,679 | 4/1981 | Tsuda et al. | 435/28 |

FOREIGN PATENT DOCUMENTS

| | | | |
|---|---|---|---|
| 321007 | 9/1934 | Italy | 260/508 |
| 54-138494 | 10/1979 | Japan | 435/11 |
| 56-42599 | 4/1981 | Japan | 435/28 |
| 56-55199 | 5/1981 | Japan | 435/28 |
| 56-61999 | 5/1981 | Japan | 435/28 |

*Primary Examiner*—Teddy S. Gron
*Attorney, Agent, or Firm*—Jacobs & Jacobs

[57] ABSTRACT

N-sulfoalkylaniline derivatives in which at least one sulfoalkyl of 2 to 4 carbon atoms is attached to the nitrogen atom which are useful as dyestuff forming substances, a composition for determining the presence of peroxides using such compounds and the process for determination of peroxides using such compounds.

9 Claims, No Drawings

N-SULFOALKYLANILINE DERIVATIVES

CROSS-REFERENCE

This is a division of Ser. No. 198,279, filed Oct. 17, 1980, now abandoned.

The present invention relates to N-sulfoalkylaniline derivatives having the general formula:

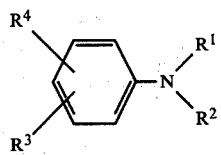

(I)

wherein $R^1$ is selected from the group consisting of hydrogen, lower alkyl, and sulfoalkyl of 2-4 carbon atoms, $R^2$ is sulfoalkyl of 2-4 carbon atoms, $R^3$ is selected from the group consisting of hydrogen, lower alkoxy, hydroxy and lower alkyl, and $R^4$ is selected from the group consisting of hydrogen, lower alkoxy, and lower alkyl, and alkali or alkaline earth salts thereof.

The term "lower alkyl" as used herein denotes a univalent residue of a straight or branched chain saturated hydrocarbon of from 1 to 6 carbon atoms, preferably from 1 to 4 carbon atoms. The term "lower alkoxy" as used herein denotes lower alkyl connected to the remainder of the molecule through an ethereal oxygen atom.

The compounds (I) of the present invention useful as dyestuff-forming substances for the determination of peroxides. The present invention also provides a composition for peroxide determination comprising a compound of formula I and a process for peroxide determination. The term "peroxide" as used herein indicates a substance having a peroxidation effect, such as hydrogen peroxide or a lipid peroxide. More particularly, the present invention relates to a composition for the determination of a peroxide, such as hydrogen peroxide or lipid peroxide, in which a peroxidase or a substance having a peroxidation effect similar to that of the peroxidase acts as catalyst in a reaction liberating a peroxide, or acts as a reactant to form a peroxide, and a processs for the determination of a peroxide in which said composition is used.

Specificity of enzymatic analysis employed for the clinical examination has recently been rated high and has come into wide use. For example, glucose, uric acid and η-cholesterol in body fluids can be determined by determining the hydrogen peroxide formed when glucose, uric acid and cholesterol in body fluids are oxidized with enzymes such as glucose oxidase, uricase and cholesterol oxidase. For example, uric acid is oxidized with uricase to form hydrogen peroxide as follows:

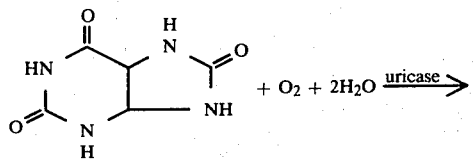

In addition, lipid peroxides in living body tissues and body fluids attract attention as a cause of diseases which may lead to the phenomena of aging and retrograde metamorphosis. Further, recently, hydrogen peroxide contained in foods has been suspected of carcinogenesis. Thus, the necessity of the determination of hydrogen peroxide formed by an oxidase in the living body, and of lipid peroxide in the living body and of hydrogen peroxide contained in foods has been recently enhanced.

For the determination of peroxides, there is generally used a composition comprising a substance having an enzymatic or non-enzymatic peroxidation effect (such as a peroxidase, a transition metal such as iron ion or a substance having a similar effect) and a substance which is changed (generally color-changed) by the peroxides in the presence of said substance. As the latter substance, i.e. so-called dyestuff-forming substance, there may be mentioned the following compounds:

(1) Monoamines such as aniline and derivatives thereof (for example, N,N-dimethylaniline) and toluidine and derivatives thereof (for example, N,N-diethyltoluidine),
(2) Diamines such as phenylenediamine and derivatives thereof, benzidine and dianisidine,
(3) Phenols such as phenol per se and derivatives thereof, e.g. cresol and naphthol,
(4) Dyestuffs such as 2,6-dichlorophenol indophenol,
(5) Triphenylmethanes such as leuco-malachite green and leuco-phenolphthalein.

They may be used either alone or in combination with a color former such as 4-aminoantipyrine or 3-methylbenzothiazolinonehydrazone.

Optimum pH distributions of enzymatic activities of enzymes which oxidatively destroy the substance in the living body to be determined are broad. Usually, the optimum pH distributes in the range of pH 5-9. For example, optimum pH of glycose oxidase, uricase and cholesterol oxidase are 5.6, 8.5 and 6.5-8.0, respectively. However, said dyestuff-forming substances, particularly monoamines and diamines, exhibit an extremely poor water solubility at said optimum pH for the enzymatic activity. Therefore, in the preparation of solutions of those dyestuff-forming substances in the prior art, the dispersion is improved by the addition of a surfactant or the precipitation of them is prevented by the addition of an organic solvent. However, even if those methods are employed, concentration of the aqueous solution changes with time and reliability in accuracy of the determination is low and there is still a fear that the surfactant and organic solvent thus added exert an ill influence on the enzymatic reaction. The accuracy can be increased by preparing the aqueous solution of dyestuff-forming substance at the time of use. This technique has, however, other problems that easiness of the operation and economicity are damaged.

Said monoamines and diamines are viscous liquids at ambient temperature and, in addition, phenol and cresol having a melting point of around 10°-40° C. are sometimes solidified at room temperature. Therefore, it is quite difficult to weigh a given amount of those compounds accurately and the preparation of the reagent solutions is troublesome.

After intensive investigations for the purpose of overcoming those defects by finding a dyestuff-forming substance which can be oxidation-condensed with a color-developer such as 4-aminoantipyrine or 3-methyl-benzothiazolinonehydrazone to give a stable determination value and a solution of which can be prepared easily, the inventors have found that compounds of general formula (I) are very excellent. Solutions of those compounds can be prepared easily, since they exhibit a high water solubility in a broad pH range and they are in solid form at ambient temperature. Further, the inventors have found that if the aqueous solution thus prepared is subjected to the oxidative condensation with 4-aminoantipyrine in the presence of a peroxidase, an indophenol type dyestuff of following formula (II) is formed, that the color is developed quite sensitively and that an excellent coloring stability lasts for a long period of time.

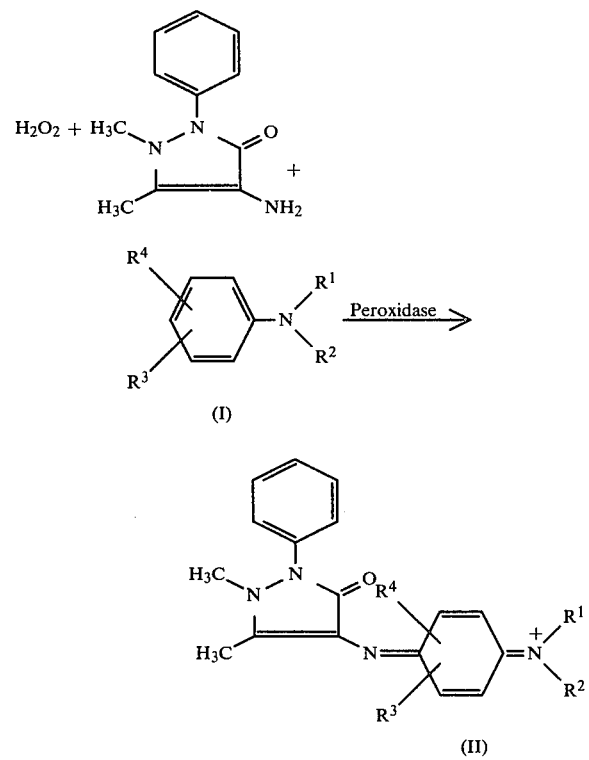

As can be seen, compounds (I) of the present invention are dyestuff-forming compounds having a high reactivity with 4-aminoantipyrine. Further, they are soluble in water and the solution has a high stability. In addition, dyestuffs obtained by the oxidative condensation of those compounds with 4-aminoantipyrine exhibit an excellent color stability. The new, useful compounds thus having excellent properties can be widely used.

Compounds of general formula (I) of the present invention can be prepared by, for example, reacting an aniline derivative of general formula (III):

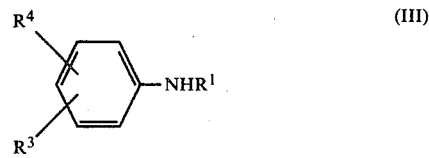

wherein $R^1$, $R^3$ and $R^4$ have the same meetings as defined above for general formula (I), with sodium bromoethanesulfonate, propanesultone or butanesultone to replace the hydrogen bonded with the nitrogen atom.

N-sulfoalkylaniline derivatives in which the sulfoalkyl radical has one carbon atom, i.e. N-sulfomethylaniline derivatives, are obtained by reacting aniline derivatives of general formula (III) with sodium hydroxymethanesulfonate. However, they are unsuitable for the dyestuff-forming substance, since aqueous solutions of those compounds are easily hydrolyzed under acidic conditions.

N-sulfoalkylaniline derivatives of 5 or more carbon atoms in the sulfoalkylmoiety have a lower specificity as dyestuff-forming substance as compared with the compounds of the present invention, and their production is economically disadvantageous as well.

Examples of compounds of general formula (I) of the present invention, their melting points, and the maximum wave lengths $\lambda_{max}$ (nm) of dyestuffs obtained by the oxidative condensation thereof with 4-aminoantipyrine are shown in Table 1. The maximum absorption wave length in the table is the maximum wave length at a pH employed for the determination but it does not indicate an optimum pH value at which the maximum absorption is attained.

As a matter of course, the compounds of the present invention are not limited to those shown in Table 1, but include all N-sulfoalkylaniline derivatives of formula I defined above. They have exhibited an excellent solubility in water and solutions of them are highly stable. Dyestuffs obtained by the oxidative condensation of N-sulfoalkylanilines in which the substituent in 4-position is a radical other than a halogen with 4-aminoantipyrine have a low color-developing sensitivity.

TABLE 1

| Compound | $R^1$ | $R^2$ | $R^3$ | $R^4$ | m.p. (°C.) (decomp.) | $\lambda_{max}$ (nm) |
|---|---|---|---|---|---|---|
| A | $C_2H_4SO_3Na$ | $C_2H_4SO_3Na$ | H | H | broad | 550 |
| B | $C_2H_5$ | $C_3H_6SO_3Ca_{\frac{1}{2}}$ | H | H | 195–200 | 562 |
| C | H | $C_3H_6SO_3H$ | 3-$CH_3$ | H | 252–254 | 535 |
| D | $C_3H_6SO_3H$ | $C_3H_6SO_3H$ | 3-$CH_3$ | H | 260 | 535 |
| E | $C_2H_5$ | $C_3H_6SO_3Ca_{\frac{1}{2}}$ | 3-$CH_3$ | H | 245–250 | 552 |
| F | $C_2H_5$ | $C_3H_6SO_3Na$ | 4-$CH_3$ | H | 190–200 | 527 |
| G | $C_4H_9$ | $C_3H_6SO_3Ca_{\frac{1}{2}}$ | H | H | 200–210 | 530 |
| H | $C_3H_6SO_3Na$ | $C_3H_6SO_3Na$ | 2-$CH_3$ | 5-$CH_3$ | 250–260 | 535 |
| I | H | $C_3H_6SO_3Na$ | 2-$OCH_3$ | H | 145–150 | 542 |
| J | H | $C_3H_6SO_3Na$ | 2-OH | H | 225–230 | 530 |
| K | H | $C_3H_6SO_3Na$ | 3-$OCH_3$ | H | 120–122 | 525 |
| L | $C_3H_6SO_3H$ | $C_3H_6SO_3H$ | 3-$OCH_3$ | H | 263–264 | 525 |

TABLE 1-continued

| Compound | $R^1$ | $R^2$ | $R^3$ | $R^4$ | m.p. (°C.) (decomp.) | $\lambda_{max}$ (nm) |
|---|---|---|---|---|---|---|
| M | $C_3H_6SO_3H$ | $C_3H_6SO_3H$ | 3-$CH_3$ | 5-$CH_3$ | 160–163 | 620 |

Maximum absorption wave length of a condensation product of phenol used in the prior art with 4-aminoantipyrine is 500 nm and that of N,N-diethylaniline is 520 nm. On the other hand, absorption wave lengths of bilirubin in body fluids and hemolyzed blood ranges broadly from ultraviolet region to around 500 nm. Therefore, a positive error might be caused in the determination values. Accordingly, for avoiding the influence thereof, it is necessary that the maximum absorption wave length is higher than 500 nm. Maximum absorption wave lengths of condensation products of N-sulfoalkylaniline derivatives of general formula (I) of the present invention with 4-aminoantipyrine are substantially higher than 530 nm and, therefore, they are not influenced by bilirubin in body fluids and hemolyzed blood. Among N-sulfoalkylaniline derivatives of general formula (I), those wherein 3- and 5-positions of the benzene ring are substituted with lower alkyl or lower alkoxy radicals are useful for the clinical examination, since their maximum absorption wave lengths are around 600 nm (for example, N,N-disulfopropyl-3,5-dimethylaniline: 620 nm, and N,N-disulfopropyl-3,5-dimethoxyaniline: 580 nm).

All compounds of general formula (I) of the present invention are in solid form at ambient temperature and, therefore, they can be used together with other necessary components as processed solids such as tablets and freeze-dried products.

Coloring stabilities of typical compounds of general formula (I) at varied pH values are shown in Table 2.

TABLE 2

| Compound ($\lambda_{max}$) | | pH 5 | pH 7 | pH 9 |
|---|---|---|---|---|
| Process of the invention | N—Ethyl-N—sulfopropyl-3-methylaniline (550 nm) | 98 | 99 | 97 |
| | N,N—Disulfopropyl-3,5-dimethoxyaniline (580 nm) | 100 | 98 | 99 |
| Prior art | Phenol (505 nm) | 62 | 98 | 99 |
| | N,N—Dimethylaniline (545 nm) | 99 | 92 | 59 |

In the above Table, coloring stability values indicate ratio (%) of (1) an absorbancy of a mixture of a sample and a reagent solution to stand at room temperature for 60 minutes to (2) an absorbancy (as 100%) after allowing the same to stand for only 5 minutes. Method of the determination of absorbancy, and compositions and method of preparation of the sample and color-developing reagent solution used for the determination were as shown below: Method of determination:

20 μl of a sample were mixed with 3 ml of a reagent solution and absorbancy of the solution at maximum absorption wave length ($\lambda_{max}$) was determined. Sample:

Hydrogen peroxide solution: $H_2O_2$; 2 mmol/l Reagent solution:

200 Units of peroxidase, 0.1 mmol of 4-aminoantipyrine and 0.5 mmol of a dyestuff-forming substance were dissolved in 100 ml of a buffer solution of varied pH to obtain a reagent solution.

Results obtained by using typical compounds of the present invention and compounds used in the prior art are shown in Table 2, which suggest that the compounds of the present invention exhibit excellent coloring stability over a broad pH range. In case phenol or dimethylaniline is to be dissolved in buffer solutions of various pH values, it is dissolved in methanol previously to the addition of the buffer solutions. On the other hand, when the compounds of the present invention are used, it is unnecessary to add a surfactant or organic solvent and the preparation of the reagent solution is easy. Results of typical dyestuff-forming substances of the present invention are shown in Table 2. It is to be understood that the dyestuff-forming substances of the present invention not shown in Table 2, i.e. other N-sulfoalkylaniline derivatives (I) than those shown in Table 2, give substantially the same effects.

In the practical use of the determination compounds and the determination method of the present invention, a combination of dyestuff-forming substance (I) with (a) a substance having an oxidation effect and (b) a color developer is employed. As substance (a), there may be mentioned peroxidase and a transition metal such as iron ion. As color developer (b), there may be mentioned 4-aminoantipyrine and 3-methylbenzothiazolinonehydrazone. It is to be noted, however, that they are merely examples but do not limit the invention.

The following examples further illustrate the present invention, which by no means limit the invention but various modifications may be made therein without departing from the spirit of the invention.

Process for the preparation of the compounds of the present invention is shown in Examples 1-3 and method of determination of peroxides using the compounds of the present invention are shown in Examples 4-6.

EXAMPLE 1

6.76 g (0.05 mol) of N-ethyl-3-methylaniline are added to 40 ml of anhydrous ethyl alcohol. Then, 6.3 g (0.05 mol) of 1,3-propanesulfone are added thereto and the mixture is refluxed under heating for 3 hours. Upon cooling, the reaction solution is neutralized with sodium hydroxide and then added with an aqueous solution of 5.5 g (0.025 mol) of calcium chloride to precipitate white crystals. The crystals are filtered out and recrystallized from water to obtain 8.8 g of calcium salt of N-ethyl-N-sulfopropyl-3-methylaniline (compound E in Table 1). Yield 62.8%.

Elementary analysis (%) as $C_{12}H_{18}NO_3SCa_{\frac{1}{2}}$

| | C | H | N |
|---|---|---|---|
| Theoretical | 52.15 | 6.56 | 5.07 |
| Found: | 52.27 | 6.57 | 5.08 |

IR Absorption characteristics ($cm^{-1}$): $\nu$—C-N< (1280), $\nu$—$SO_3$ (1070), $\nu$ aromatic ring (1600).

EXAMPLE 2

A mixture solution comprising 12 g of N-ethylaniline, 12 g of 1,3-propanesultone and 30 ml of methyl alcohol is refluxed under heating for 3 hours. Upon cooling, the mixture is neutralized to precipitate crystals of calcium chloride salt thereof. After purification with water, 12.5 g of calcium salt of N-ethyl-N-sulfopropylaniline (compound B in Table 1) are obtained. Yield 48.0%.

Elementary analysis (%) as $C_{11}H_{16}NO_3SCa_{\frac{1}{2}}$:

|  | C | H | N |
| --- | --- | --- | --- |
| Theoretical: | 50.36 | 6.15 | 5.34 |
| Found: | 49.98 | 6.10 | 5.29 |

IR Absorption characteristics $(cm^{-1})$: $\nu$—C-N<(1280), $\nu$—SO$_3$ (1060), $\nu$aromatic ring (1600).

EXAMPLE 3

A mixture solution comprising 10 g of 2-methoxyaniline, 10 g of 1,3-propanesultone and 30 ml of methyl alcohol is refluxed under heating for 2 hours. Upon cooling, the mixture is neutralized with sodium hydroxide. The solution is concentrated. After cooling, crystals formed are filtered out and recrystallized from a solvent mixture of water and methanol to obtain 6.9 g of sodium salt of N-sulfopropyl-2-methoxyaniline (compound I in Table 1). Yield: 31.9%.

Elementary analysis (%) as $C_{10}H_{14}NO_4SNa$:

|  | C | H | N |
| --- | --- | --- | --- |
| Theoretical: | 44.94 | 5.28 | 5.24 |
| Found: | 45.31 | 5.32 | 5.28 |

IR Absorption characteristics $(cm^{-1})$: $\nu$—NH— (3550), $\nu$—SO$_3$ (1050), $\nu$aromatic ring (1600).

EXAMPLE 4

400 Units of glucose oxidase, 200 units of peroxidase, 30 mg of 4-aminoantipyrine and 100 mg of sodium N-ethyl-N-sulfopropylaniline are dissolved in 100 ml of 0.1 M acetic acid buffer solution (pH 5.6) to obtain a color-developing solution.

20 μl of serum are charged in a test tube, 3.0 ml of said color-developing solution are added thereto and the reaction is carried out at 37° C. Thereafter, absorbancy is determined using the results of blank test as control. Glucose concentration in he serum is calculated with reference to a calibration curve previously prepared by a known method.
Standard Solution: Glucose 200 mg/dl
Sensitivity: 0.586.

EXAMPLE 5

0.3 Gram of acetic acid, 40 mg of aminoantipyrine, 5 mg of ammonium ferrous sulfate and 100 mg of sodium N-ethyl-N-sulfopropyl-3-methylaniline are dissolved in 100 ml of water to obtain a color developing solution.

4.0 Milliliters of isopropanol are a-ded to 200 μl of a sample. The mixture is stirred by means of a mixer twice at an interval of 5 seconds and then subjected to centrifugal separation at 2000 rpm. for 10 minutes. 3.0 Milliliters of a supernatant liquid are placed in a test tube and added with 1.0 ml of the reagent solution. After carrying out the reaction at 37° C., absorbancy of the sample at 550 nm is determined employing the results of blank test as control. Lipid peroxide concentration in the serum is calculated with reference to a calibration curve previously prepared by a known method.
Standard solution: t-Butyl hydroperoxide 12 μg/ml
Sensitivity: 0.430.

EXAMPLE 6 (Determination of hydrogen peroxide in a food)

A sample is divided finely. 40 Grams of thus divided fine sample are added with 60–80 ml of water and the whole is homogenized for 5–10 minutes. Thus treated sample is transferred into a 250 ml measuring flask by washing the contents of the flask with water. Water is added thereto to make the total volume 250 ml. The mixture is subjected to the centrifugal separation. The supernatant liquid is separated out by filtration to obtain a sample solution.

20 Milligrams of 4-aminoantipyrine, 5 mg of ammonium ferrous sulfate and 100 mg of sodium N,N-disulfopropyl 3,5-dimethylaniline are dissolved in 0.1 M phosphate buffer solution (pH 7) to obtain 100 ml of a reagent solution.

The sample solution (200 μl) are placed in a test tube. 3.0 Milliliters of the reagent solution are added thereto. Absorbancy at 620 nm is determined employing the results of blank test as control. Hydrogen peroxide concentration in the food is calculated with reference to a calibration curve previously prepared by a known method.
Standard solution: Hydrogen peroxide 1.32 mg/dl
Sensitivity: 0.151.

What is claimed:

1. A composition for determing the presence of peroxides, comprising a crystalline compound of the formula (I):

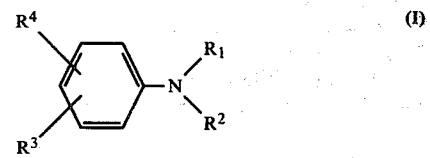

wherein
$R^1$ is selected from the group consisting of hydrogen, lower alkyl and sulfoalkyl of 2–4 carbon atoms;
$R^2$ is sulfoalkyl of 2–4 carbon atoms;
$R^3$ is selected from the group consisting of hydrogen, hydroxy and lower alkyl and lower alkoxy; and
$R^4$ is selected from the group consisting of hydrogen, lower alkoxy and lower alkyl, or the alkali metal or alkaline earth metal salt thereof, and a color-developer substance that will react with hydrogen peroxide selected from the groups consisting of 4-aminoantipyrine and 3-methyl-benzothiazolinonehydrazone and a said compound to form a dyestuff in the presence of peroxidase or a transition metal.

2. A composition according to claim 1 wherein the compound of the formula (I) is the calcium salt of N-ethyl-N-sulfopropyl-3-methylaniline.

3. A composition according to claim 1 wherein the compound of the formula (I) is the calcium salt of N-ethyl-N-sulfopropylaniline.

4. A composition according to claim 1 wherein the compound of the formula (I) is the sodium salt of N-sulfopropyl-2-methoxyaniline.

5. A process for determination of peroxides, which comprises adding to a sample containing an unknown quantity of a material capable of liberating peroxide upon peroxidation, a crystalline compound of the formula (I):

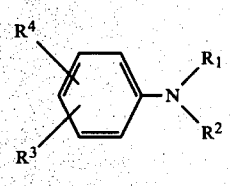

wherein
- R¹ is selected from the group consisting of hydrogen, lower alkyl and sulfoalkyl of 2-4 carbon atoms;
- R² is sulfoalkyl of 2-4 carbon atoms;
- R³ is selected from the group consisting of hydrogen, hydroxy and lower alkyl and lower alkoxy; and
- R⁴ is selected from the group consisting of hydrogen, lower alkoxy and lower alkyl, or the alkali metal or alkaline earth metal salt thereof, a color-developer substance that will react in an oxidative-condensation with said compound to form a dyestuff and a peroxidase or a transition metal, and measuring the absorbency of the solution at maximum absorption.

6. The process according to claim 5, wherein said color developer is 4-aminoantipyrine or 3-methylbenzothiazolinonehydrazone.

7. A process according to claim 5 wherein the compound of the formula (I) is the calcium salt of N-ethyl-N-sulfopropyl-3-methylaniline.

8. A process according to claim 5 wherein the compound of the formula (I) is the calcium salt of N-ethyl-N-sulfopropylaniline.

9. A process according to claim 5 wherein the compound of the formula (I) is the sodium salt of N-sulfopropyl-2-methoxyaniline.

* * * * *